US00PP29466P3

(12) United States Plant Patent
Kordes

(10) Patent No.: US PP29,466 P3
(45) Date of Patent: Jul. 10, 2018

(54) SHRUB ROSE PLANT NAMED 'KORBAYMUN'

(50) Latin Name: *Rosa hybrida*
Varietal Denomination: KORbaymun

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 6 days.

(21) Appl. No.: 15/330,134

(22) Filed: Aug. 12, 2016

(65) Prior Publication Data

US 2018/0049357 P1 Feb. 15, 2018

(51) Int. Cl.
*A01H 5/02* (2018.01)

(52) U.S. Cl.
USPC ..... Plt./102
CPC ..... *A01H 5/0222* (2013.01)

(58) Field of Classification Search
USPC ..... Plt./101, 102, 103, 107, 108, 130, 132, Plt./141, 143
See application file for complete search history.

(56) References Cited

PUBLICATIONS

HelpMeFind Roses, Clematis and Peonies. http://www.helpmefind.com/gardening/l.php?l=2.76415.2. citation for Korbaymun. retrieved Oct. 10, 2017. 1 page.*

* cited by examiner

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

'KORbaymun' is a new and distinct variety of *Rosa hybrida* which is characterized by the combination of an upright and bushy growth habit, a moderately vigorous rate of growth, panicles bearing one to five white flowers suffused with red and irregularly striped and margined red, semi-double flowers with light fragrance, and excellent resistance to common rose diseases. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORbaymun'.

STATEMENT REGARDING PRIOR DISCLOSURES BY THE INVENTOR UNDER 37 C.F.R. 1.77(B)(6)

The first public disclosure of the claimed plant was made on Aug. 21, 2015 at a public ceremony in Schuttringen, Luxembourg where cut flower stems were displayed by the inventor, but not sold or otherwise transferred. The claimed plant was not specifically identified by name in the display. 'KORbaymun' was not publically available or sold prior to one year before the date of the instant application.

BACKGROUND OF THE INVENTION

Parentage: The *Rosa hybrida* variety 'KORbaymun' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth habit and uniform flowering; and
2. Abundant, recurrent white flowers suffused with red; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORbaymun' from all other varieties known to the inventor.

'KORbaymun' is a seedling selection which resulted from the controlled pollination of *Rosa hybrida* 'KORschwill' (U.S. Plant Pat. No. 23,122), the seed parent, and *Rosa hybrida* 'MACcastler' (unpatented), the pollen parent, during the summer of 2007. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2008 from the seedling beds due to its superior characteristics and asexually propagated for further evaluation. This new and distinctive rose variety was given the name 'KORbaymun'.

Asexual Reproduction: 'KORbaymun' was first asexually propagated by bud grafting in July of 2008 at the inventor's nursery in Klein Offenseth-Sparrieshoop, Germany. Subsequently, 'KORbaymun' has been successfully propagated by stem cuttings and bud grafting in Jackson County, Oreg. These initial and other subsequent propagations conducted in controlled environments demonstrate that 'KORbaymun' reproduces true to type in successive generations of asexual reproduction.

SUMMARY OF THE INVENTION

The following characteristics have been repeatedly observed and represent the distinguishing characteristics of the new *Rosa hybrida* cultivar 'KORbaymun'. These traits, in combination, distinguish 'KORbaymun' as a new and distinct cultivar.

1. *Rosa hybrida* 'KORbaymun' exhibits a moderately vigorous growth rate; and
2. *Rosa hybrida* 'KORbaymun' exhibits an upright and bushy growth habit; and
3. *Rosa hybrida* 'KORbaymun' exhibits panicles bearing one to five white flowers suffused with red and irregularly striped and margined red; and
4. *Rosa hybrida* 'KORbaymun' exhibits medium, double flowers with a light fragrance; and
5. *Rosa hybrida* 'KORbaymun' exhibits excellent resistance to rust, black spot disease, *Botrytis* and powdery mildew.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORbaymun', taken from a three year old plant.

DETAILED BOTANICAL DESCRIPTION

The following is a detailed botanical description of a new and distinct variety of *Rosa hybrida* known as 'KORbaymun', based upon observations made in June of 2016 from nine month old, field-grown plants in Jackson County, Oreg. Those skilled in the art will appreciate that certain characteristics will vary with older or, conversely, with younger plants. 'KORbaymun' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORbaymun' and comparisons with the parents and closest known comparator variety of *Rosa hybrida* are provided below.

General plant description:

*Growth rate*.—Moderately vigorous.

*Growth habit*.—Upright and bushy.

*Mature dimensions*.—90 cm tall and 45 cm wide, on average.

*Cold hardiness*.—Grown successfully in USDA Hardiness Zones 5.

*Propagation*.—Stem cuttings and bud grafting.

*Disease resistance*.—Excellent resistance to powdery mildew (*Sphaerotheca pannosa*), blackspot (*Diplocarpon rosae*), rust (*Phragmidium* sp.) and *Botrytis* diseases under normal growing conditions in Jackson County, Oreg.

Root system:

*Type*.—Fibrous root system.

*Branching*.—Freely branched.

*Density*.—Moderately dense.

*Color*.—Greyed-yellow Group 161D.

*Distribution*.—Roots distributed evenly throughout the soil profile, from shallow to deep.

Stems:

*Stem color*.—Young stems are Yellow-Green Group 146B; mature stems are Yellow-Green Group 146A.

*Anthocyanin intonations*.—Intonations of Greyed-Red Group 178A are present on young stems.

*Stem surface texture*.—Both juvenile and mature stems are smooth.

*Stem dimensions*.—Typical mature stems are approximately 40 cm long and 6 to 8 mm in diameter.

*Prickles*.—Incidence — Typically 10 prickles per 10 cm of stem, on average. Size — Average length is 8 mm long. Immature prickle color — Greyed-Red Group 181B. Mature prickle color — Greyed-Red Group 179C. Shape — Deeply concave. Texture — Smooth.

Leaves:

*Arrangement*.—Imparipinnate compound leaves; mature axillary leaves consisting of 7 leaflets.

*Attachment*.—Petiolate.

*Dimensions*.—180 mm long and 190 mm wide.

*Abundance*.—Average; approximately 90 leaves.

*Stipules*.—

*Size*.—25 mm long and 10 mm wide.

*Stipule color*.—Yellow-Green Group 146A.

*Anthocyanin intonations*.—Greyed-Purple Group 183D intonations are present on the center rib of the adaxial surface and also present on the adaxial stipule surfaces.

*Stipitate glands*.—Abundant stipitate glands are present on the abaxial surfaces and also along the margins.

*Margins*.—With stipitate glands at the apex.

*Texture, adaxial surfaces*.—Glabrous.

*Texture, abaxial surfaces*.—Leathery.

*Apex*.—Apiculate.

*Base*.—Winged.

*Petiole*.—Length — Average of 8 to 10 mm. Diameter — Average of 3 to 4 mm. Petiole color, adaxial surface — Yellow-Green Group 146B. Petiole color, abaxial surface — Yellow-Green Group 146B. Anthocyanin intonations — Greyed-Purple Group 183B intonations are present on the adaxial surface; light intonations are present on the abaxial surface. Margins — With many stipitate glands. Prickles — Large prickles are present on the abaxial surface. Stipitate glands — Abundance of stipitate glands are present on the abaxial surface. Texture — Glabrous. Strength — Strong.

*Rachis*.—Length — Average 20 mm. Diameter — Average 3.0 to 4.0 mm. Color — Yellow-Green Group 146C. Anthocyanin intonations — Intonations of Greyed-Purple Group 183B are present on the adaxial surface. Margins — With stipitate glands.

Prickles — A few small prickles on the abaxial surface with a large, prominent prickle at the point of leaf attachment. Stipitate glands — Abundance of stipitate glands are present on the upper margins with fewer glands on the lower margins. Texture — Glabrous.

*Leaflets*.—Dimensions — Average size of the terminal leaflet is 75 mm long and 40 mm wide. Shape — Obovate. Apex — Acute. Base — Obtuse. Margins — Serrated; slightly undulated. Luster, texture and pubescence; adaxial surface — Semi-glossy, smooth and glabrous. Luster, texture and pubescence; abaxial surface — Matte, leathery and glabrous; small prickles are present at the midrib. Juvenile foliage color, adaxial surface — Yellow-Green Group 147A. Juvenile foliage color, abaxial surface — Yellow-Green Group 147C. Mature foliage color, adaxial surface — Yellow-Green Group 146A. Mature foliage color, abaxial surface — Yellow-Green Group 147B. Anthocyanin intonations — Very strong intonations of Greyed-Purple Group 183A are present on both surfaces of the juvenile foliage; slight intonations of Greyed-Purple Group 183A are present on the abaxial surface of the mature foliage. Venation — Reticulate. Petiolule — Dimensions — 3.0 mm long and 1.0 mm in diameter. Petiolule color, adaxial surface — Yellow-Green Group 146D. Petiolule color, abaxial surface — Yellow-Green Group 147C. Anthocyanin intonations — Intonations of Greyed-Purple Group 183A are present on the margins. Prickles — A few small prickles are present on the abaxial surface. Texture, adaxial and abaxial surfaces — Smooth.

Inflorescence:

*Inflorescence type*.—Panicles which bear 1 to 5 flower buds. Flowers are held upright.

*Blooming habit*.—Recurrent; floriferous.

*Size*.—24 cm tall and 16 cm wide, on average.

*Peduncle*.—Length — 100 to 130 mm average length. Diameter — 5.0 to 7.0 mm average diameter. Color — Yellow-Green Group 146B. Anthocyanin intonations — None. Strength — Strong. Surface — Glabrous.

Flowering laterals: Present below the initiation of inflorescence. Generally 1 to 2 flowering laterals are present, with 1 to 2 flowers per flowering shoot.

Bud:

*Bud form*.—Short; pointed ovoid.

*Size*.—Upon opening, 35 mm in length from base of receptacle to distal end of bud and 20 mm diameter at its widest point.

*Texture*.—Smooth.

*Color, as sepals first unfold*.—Red Group 43B.

*Color when one-quarter open, inner side*.—Marginal zone — Red Group 41B. Middle zone — White Group N155D. Basal zone — White Group N155D.

*Color when one-quarter open, outer side*.—Marginal zone — Red Group 52A, with irregular areas of White Group N155D. Middle zone — Red Group 52A, with irregular areas of White Group N155D. Basal zone — Red Group 52A, with irregular areas of White Group N155D.

Flower:

*Pedicel*.—Length — 70 to 120 mm average length. Diameter — 2.0 to 4.0 mm average diameter. Color — Yellow-Green Group 147B. Anthocyanin intonations — Greyed-Orange Group 175D. Strength — Strong. Surface — Smooth, with stipitate glands.

*Calyx*.—General — Comprised of five polysepalous sepals, with moderate foliaceous appendages present on three sepals. Diameter of calyx — 45 mm, at anthesis.

*Sepals*.—Color, upper surface — Yellow-Green Group 147C. Color, lower surface — Yellow-Green Group 146A. Anthocyanin intonations — Intonations of Greyed-Purple Group 183C are present on the lower surface. Size — 20 mm long and 9 mm wide, on average. Apex — Cirrose and apiculate apices are observed. Base — Flat at union with receptacle. Quantity — Five. Upper surface — Pubescent. Lower surface — Lightly pubescent, with stipitate glands. Margins — Pubescent, with stipitate glands.

*Corolla*.—Habit; type — Double. General shape of corolla — Cup-open; shallow. Shape of corolla when viewed from the side — Upon opening, upper portion — Flat. Upon opening, lower portion — Flat. Open flower, upper portion — Flattened convex. Open flower, lower portion — Flattened convex. Dimensions — Medium size for a shrub rose. When open, the average flower diameter is 75 mm and the average flower height is 30 mm. Fragrance — Light fragrance. Duration — On the plant for 3 to 5 days. Senesced petals drop away cleanly. Petals — Petal count — Exhibits double flowers with 20 to 22 petals under normal conditions. Petal reflex — Petals are somewhat reflexed. Timing of petal reflex — Simultaneous. Petal margin — Entire. Petal shape — Obovate. Apex — Obtuse. Base — Obtuse. Dimensions — 40 to 45 mm long and 40 to 50 mm wide. Texture, inner surface — Smooth. Texture, outer surface — Smooth. Petal color, upon opening — Outermost petals, inner surface — Primarily Red Group 46A to 46C with irregular areas of White Group 155C. Outermost petals, outer surface — Predominantly White Group N155B with stripes of Red Group 47A to 47C. Innermost petals, inner surface — White Group 155D and lightly striped with Red Group 52C. Innermost petals, outer surface — White Group 155D with irregular striping of Red Group 49B. Basal petal spots, upon opening — No distinctive coloration at the petal base. Petal color, after opening — Outermost petals, inner surface — White Group N155B, and striped with Red Group 50A. Outermost petals, outer surface — White Group N155B, and striped with a mixture of Red-Purple Group 58B and 58C. Innermost petals, inner surface — White Group 155C, and striped with Red Group 47C. Innermost petals, outer surface — White Group 155C, and striped with Red Group 53C. Basal petal spots, after opening — No distinctive coloration at the petal base. General Tonality — On open flower, Red Group 46D. No change in general tonality at the end of the fifth day; thereafter the general tonality is White Group 155B margined with Red Group 53C. Petaloids — Quantity — 7 petaloids per flower, on average. Dimensions — Variable; approximately 12 to 20 mm long and 4 to 8 mm wide. Color, inner surface — Red Group 43B to Red Group 54A. Color, outer surface — White Group 155C and striped Red Group 46D. Margins — Entire and indented. Shape — Cuneate. Apex — Obtuse. Base — Attenuate. Texture, inner and outer surfaces — Smooth.

Reproductive organs:

*Stamens*.—Quantity — Approximately 50, on average, arranged around the styles. Anthers — Shape — Reniform. Dimensions — 3.0 mm long and 0.5 mm wide, on average. Color — White Group 155A with intonations of Red Group 47C. Pollen — Present; moderately abundant. Color is Yellow Group 8B. Filaments — Color — Green-Yellow Group 1A. Length — 6 mm.

*Pistils*.—Quantity — Average; approximately 20. Stigmas — Size — 0.5 mm. Location — Inferior in position to anthers. Color — Yellow-Green Group 154C. Styles — Length — Approximately 4.0 mm long. Color — Yellow-Green 145D.

*Ovary*.—Dimensions — 7 mm long and 4 mm in diameter. Color — Green-White Group 157C.

*Receptacle*.—Shape — Funnel-shaped. Dimensions — Approximately 10 mm high and 8 mm wide. Color — Yellow-Green Group 144B with intonations of Greyed-Purple Group 184A. Texture — Smooth; glabrous; lacking stipitate glands.

Hips and seed formation: Not observed to date.

COMPARISONS WITH THE PARENTS

The new rose plant may be distinguished from its seed parent, *Rosa hybrida* 'KORschwill', by the following combination of characteristics:

1. 'KORbaymun' exhibits white flowers suffused with red and irregularly striped and margined red, whereas the seed parent exhibits red flowers.
2. 'KORbaymun' grows to approximately 90 cm tall, whereas the seed parent grows to approximately 70 cm tall.

The new rose plant may be distinguished from its pollen parent, *Rosa hybrida* 'MACcastler', by the following combination of characteristics:

1. 'KORbaymun' exhibits cupped flowers, whereas the pollen parent exhibits pointed, elegant flowers.
2. 'KORbaymun' exhibits excellent disease resistance, whereas the pollen parent exhibits average disease resistance.

COMPARISON WITH THE MOST SIMILAR *ROSA* CULTIVAR KNOWN TO THE INVENTOR

For a comparison, several physical characteristics of the *Rosa hybrida* variety 'KORumneza', a rose variety from the same inventor which is described and illustrated in U.S. Plant Pat. No. 26,309, are compared to 'KORbaymun' in Chart 1.

CHART 1

| Characteristic | 'KORbaymun' | 'KORumneza' |
|---|---|---|
| Corolla diameter at anthesis. | 75 mm. | 100 mm. |
| Petal count. | 20 to 22. | 15. |
| Size of prickles on stems. | 8 mm. | 4 mm. |

That which is claimed:

1. A new and distinct variety of rose plant named 'KORbaymun', as described and illustrated herein.

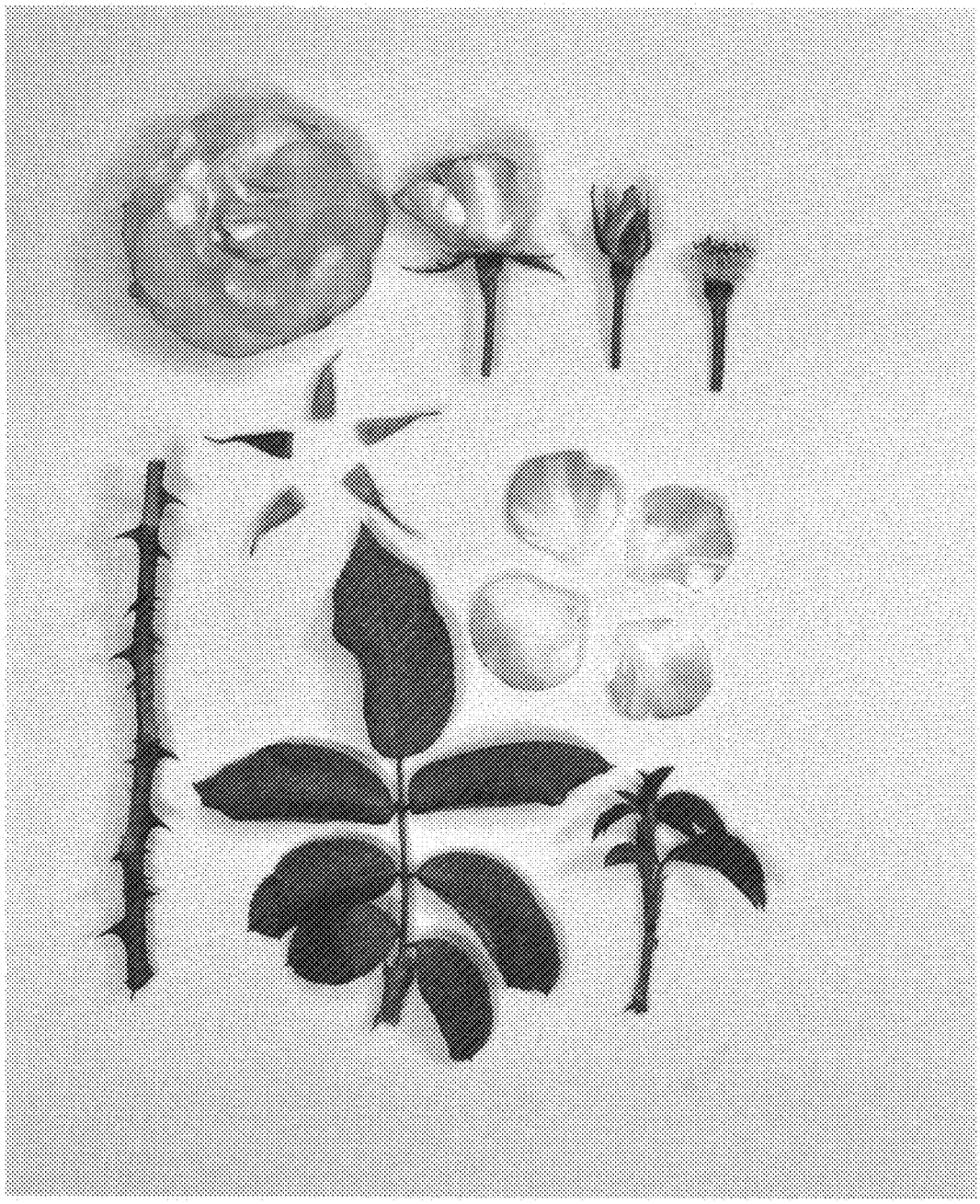

* * * * *